US012584119B2

(12) United States Patent
Lassila et al.

(10) Patent No.: US 12,584,119 B2
(45) Date of Patent: Mar. 24, 2026

(54) VARIANT ALPHA-AMYLASES HAVING AMINO ACID SUBSTITUTIONS THAT LOWER THE PKA OF THE GENERAL ACID

(71) Applicant: DANISCO US INC, Palo Alto, CA (US)

(72) Inventors: Jonathan K. Lassila, Palo Alto, CA (US); Patrica Tran, Palo Alto, CA (US)

(73) Assignee: DANISCO US INC, Palo Alto, CA (US)

( * ) Notice: Subject to any disclaimer, the term of this patent is extended or adjusted under 35 U.S.C. 154(b) by 1084 days.

(21) Appl. No.: 17/264,531

(22) PCT Filed: Jul. 30, 2019

(86) PCT No.: PCT/US2019/044254
§ 371 (c)(1),
(2) Date: Jan. 29, 2021

(87) PCT Pub. No.: WO2020/028443
PCT Pub. Date: Feb. 6, 2020

(65) Prior Publication Data
US 2023/0174962 A1        Jun. 8, 2023

Related U.S. Application Data

(60) Provisional application No. 62/712,446, filed on Jul. 31, 2018.

(51) Int. Cl.
*C12N 9/26*        (2006.01)
*C11D 3/386*        (2006.01)

(52) U.S. Cl.
CPC ........... *C12N 9/2414* (2013.01); *C11D 3/386* (2013.01); *C12Y 302/01001* (2013.01); *C07K 2299/00* (2013.01)

(58) Field of Classification Search
CPC ................. C12N 9/2414; C11D 3/386; C12Y 302/01001
See application file for complete search history.

(56) References Cited

U.S. PATENT DOCUMENTS

| | | | |
|---|---|---|---|
| 11,441,139 B2 * | 9/2022 | Lassila ................. | C12N 9/2417 |
| 11,920,170 B2 * | 3/2024 | Cuevas .......... | C12Y 302/01001 |
| 2008/0293607 A1 | 11/2008 | Jones | |
| 2016/0348084 A1 | 12/2016 | Andersen et al. | |
| 2021/0122998 A1 * | 4/2021 | Jackson ............. | C11D 3/38618 |
| 2023/0227803 A1 * | 7/2023 | Lassila .................... | C12P 19/14 |
| | | | 435/201 |
| 2023/0265358 A1 * | 8/2023 | Bell-Rusiewicz ... | C11D 3/3932 |
| | | | 510/392 |

FOREIGN PATENT DOCUMENTS

| | | | | |
|---|---|---|---|---|
| WO | 9418314 A1 | 8/1994 | | |
| WO | 9510603 A1 | 4/1995 | | |
| WO | 9526397 A1 | 10/1995 | | |
| WO | 9623873 A1 | 8/1996 | | |
| WO | 9623874 A1 | 8/1996 | | |
| WO | 9741213 A1 | 11/1997 | | |
| WO | 9813481 A1 | 4/1998 | | |
| WO | 9919467 A1 | 4/1999 | | |
| WO | 9923211 A1 | 5/1999 | | |
| WO | 9942567 A1 | 8/1999 | | |
| WO | 9946399 A1 | 9/1999 | | |
| WO | 0029560 A1 | 5/2000 | | |
| WO | 0060059 A2 | 10/2000 | | |
| WO | 0060060 A2 | 10/2000 | | |
| WO | 0114532 A2 | 3/2001 | | |
| WO | 0166712 A2 | 9/2001 | | |
| WO | 2001064852 A1 | 9/2001 | | |
| WO | 0188107 A2 | 11/2001 | | |
| WO | 0196537 A2 | 12/2001 | | |
| WO | 0210355 A2 | 2/2002 | | |
| WO | 02092797 A2 | 11/2002 | | |
| WO | 2004055178 A1 | 7/2004 | | |
| WO | 2006000058 A1 | 1/2006 | | |
| WO | 2006002643 A2 | 1/2006 | | |
| WO | 2009061380 A1 | 5/2009 | | |
| WO | 2010115028 A2 | 10/2010 | | |
| WO | WO 2013/063460 A2 * | 5/2013 | ............ | A21D 8/042 |
| WO | 2013184577 A1 | 12/2013 | | |
| WO | 2014099523 A1 | 6/2014 | | |
| WO | 2014164777 A1 | 10/2014 | | |
| WO | 2015077126 A1 | 5/2015 | | |
| WO | 2017114891 A1 | 7/2017 | | |
| WO | 2018184004 A1 | 10/2018 | | |

OTHER PUBLICATIONS

Nielsen et al., Protein Engineering, (2001), vol. 14, No. 7, pp. 505-512. (Year: 2001).*
Hwang et al., Molecules and Cells. (1997), vol. 7, No. 2, pp. 251-258. (Year: 1997).*
Stam et al., Protein Engineering, Design & Selection. (2006), vol. 10, No. 12, pp. 555-562. (Year: 2006).*
Priyadharshini et al., J. Microbiol. Biotechnol. (2010), vol. 20(12), pp. 1696-1701. (Year: 2010).*
Nielsen J E et al: "Protein engineering of bacterial alpha-amylases", Biocimica et Biophysica A ET Biophysica ACTA. Protein Structure and Molecular Enzymology, Elsevier, Amsterdam; NL, vol. 1543, No. 2, Dec. 29, 2000 (Dec. 29, 2000), pp. 253-274, XP004279109.
Suzuki, et al., "Amino Acid Residues Stabilizing a Bacillus a-Amylase against Irreversible Thermoinactivation", Jrnl. of Biological Chemistry, vol. 264, Issue 32, Nov. 15, 1989, pp. 18933-18938.

* cited by examiner

*Primary Examiner* — Lianko G Garyu
*Assistant Examiner* — Claudia Espinosa

(57) ABSTRACT

Disclosed are compositions and methods relating to variant α-amylases. The variant α-amylases are useful, for example, for starch liquefaction and saccharification, cleaning starchy stains, textile desizing, baking and brewing.

12 Claims, 4 Drawing Sheets
Specification includes a Sequence Listing.

```
Amy707      HHNGTNGTMMQYFEWYLPNDGNHWNRLNSDASNLKSKGITAVWIPPAWKGASQNDVGYGA
AA560       HHNGTNGTMMQYFEWYLPNDGNHWNRLRSDASNLKDKGISAVWIPPAWKGASQNDVGYGA
BspAmy24    HHNGTNGTMMQYFEWHLPNDGQHWNRLRNDAANLKNLGITAVWIPPAWKGTSQNDVGYGA
            *************:*****:*****..**:***. **:***********:*********

Amy707      YDLYDLGEFNQKGTVRTKYGTRSQLQAAVTSLKNNGIQVYGDVVMNHKGGADATEMVRAV
AA560       YDLYDLGEFNQKGTIRTKYGTRNQLQAAVNALKSNGIQVYGDVVMNHKGGADATEMVRAV
BspAmy24    YDLYDLGEFNQKGTIRTKYGTRSQLQSAIASLQNNGIQVYGDVVMNHKGGADGTEWVQAV
            **************:*******.***:*: :*:.****************** *.:**

Amy707      EVNPNNRNQEVTGEYTIEAWTRFDFPGRGNTHSSFKWRWYHFDGVDWDQSRRLNNRIYKF
AA560       EVNPNNRNQEVSGEYTIEAWTKFDFPGRGNTHSNFKWRWYHFDGVDWDQSRKLNNRIYKF
BspAmy24    EVNPSNRNQEVTGEYTIEAWTKFDFPGRGNTHSSFKWRWYHFDGTDWDQSRQLNNRIYKF
            ****.******:*******::***********.*********.******:.********

Amy707      RGHGKAWDWEVDTENGNYDYLMYADIDMDHPEVVNELRNWGVWYTNTLGLDGFRIDAVKH
AA560       RGDGKGWDWEVDTENGNYDYLMYADIDMDHPEVVNELRNWGVWYTNTLGLDGFRIDAVKH
BspAmy24    RGTGKAWDWEVDTENGNYDYLMYADVDMDHPEVINELRRWGVWYTNTLNLDGFRIDAVKH
            ** **.*******************:*******:****.*********.**********

Amy707      IKYSFTRDWINHVRSATGKN-MFAVAEFWKNDLGAIENYLQKTNWNHSVFDVPLHYNLYN
AA560       IKYSFTRDWINHVRSATGKN-MFAVAEFWKNDLGAIENYLNKTNWNHSVFDVPLHYNLYN
BspAmy24    IKYSFTRDWLNHVRSTTGKNNMFAVAEFWKNDLGAIENYLHKTNWNHSVFDVPLHYNLYN
            *********:*****:.**** ******************:.*******************

Amy707      ASKSGGNYDMRNIFNGTVVQRHPSHAVTFVDNHDSQPEEALESFVEEWFKPLAYALTLTR
AA560       ASKSGGNYDMRQIFNGTVVQRHPMHAVTFVDNHDSQPEEALESFVEEWFKPLAYALTLTR
BspAmy24    ASKSGGNYDMRQILNGTVVSKHPIHAVTFVDNHDSQPAEALESFVEAWFKPLAYALILTR
            ***********:*:*****..:**  ***********.********* ******** ***

Amy707      EQGYPSVFYGDYYGIPTHGVPAMRSKIDPILEARQKYAYGKQNDYLDHHNIIGWTREGNT
AA560       EQGYPSVFYGDYYGIPTHGVPAMKSKIDPILEARQKYAYGRQNDYLDHHNIIGWTREGNT
BspAmy24    EQGYPSVFYGDYYGIPTHGVAAMKGKIDPILEARQKYAYGTQHDYLDHHNIIGWTREGNS
            ********************.**:.***************** *:*****************:

Amy707      AHPNSGLATIMSDGAGGSKWMFVGRNKAGQVWSDITGNRTGTVTINADGWGNFSVNGGSV
AA560       AHPNSGLATIMSDGAGGNKWMFVGRNKAGQVWTDITGNRAGTVTINADGWGNFSVNGGSV
BspAmy24    AHPNSGLATIMSDGPGGSKWMYVGRHKAGQVWRDITGNRTGTVTINADGWGNFSVNGGSV
            **************.**.***:***:******.*******.********************

Amy707      SIWVNK (SEQ ID NO: 2)
AA560       SIWVNK (SEQ ID NO: 3)
BspAmy24    SIWVNK (SEQ ID NO: 1)

VARIANT ALPHA-AMYLASES HAVING AMINO ACID SUBSTITUTIONS THAT LOWER THE PKA OF THE GENERAL ACID

CROSS-REFERENCE TO RELATED APPLICATIONS

The present application claims priority to U.S. Provisional Patent Application Ser. No. 62/712,446, filed Jul. 31, 2018, which is hereby incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named 20210820_NB41518USPCT_Sequence_ST25 created on Aug. 20, 2021 and having a size of 13 kilobytes and is filed concurrently with the specification. The sequence listing contained in this ASCII formatted document is part of the specification and is herein incorporated by reference in its entirety.

TECHNICAL FIELD

Disclosed are compositions and methods relating to variant α-amylases. The variant α-amylases are useful, for example, for starch liquefaction and saccharification, cleaning starchy stains, textile desizing, baking and brewing.

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

α-amylases hydrolyze starch, glycogen, and related polysaccharides by cleaving internal α-1,4-glucosidic bonds at random. α-amylases, particularly from Bacilli, have been used for a variety of different purposes, including starch liquefaction and saccharification, textile desizing, starch modification in the paper and pulp industry, brewing, baking, production of syrups for the food industry, production of feed-stocks for fermentation processes, and in animal feed to increase digestibility. These enzymes can also be used to remove starchy soils and stains during dishwashing and laundry washing.

Numerous α-amylases are commercially available and the enzymes have become almost indispensable for many applications. Competition among enzyme manufacturers is fierce and drives a neverending competition to develop ever-improving enzymes. The need exists to develop new ways to improve α-amylases using approaches beyond random mutagenesis and high throughput screening.

SUMMARY

The present compositions and methods relate to variant α-amylase polypeptides, and methods of use, thereof, and methods for designing variant α-amylases. Aspects and embodiments of the present compositions and methods are summarized in the following separately-numbered paragraphs:

1. In one aspect, a recombinant variant of a parental Family 13 α-amylase is provided, the variant having at least 60% amino acid sequence identity to the amino acid sequence of SEQ ID NO: 1 and having an amino acid mutation in an amino acid residue that lines the N-terminal side of the core β-barrel structure of the α-amylase that results in the variant having an amino acid residue that is different from the naturally occurring amino acid in the parent α-amylase, and which results in reduction of the apparent $pK_a$ value of the general acid and an increase in the activity of the variant at a pH between about 8.5 and 10.5.

2. In some embodiments of the variant α-amylase of paragraph 1, the ratio of the activity at pH 8.5 compared to the activity at pH 10.5 for the variant divided by the ratio of the activity at pH 8.5 compared to the activity at pH 10.5 of an otherwise identical α-amylase lacking the amino acid mutation in an amino acid residue that lines the N-terminal side of the core β-barrel structure of the α-amylase is greater than 1, greater than 2, greater than 3, or greater than 4.

3. In some embodiments, the variant α-amylase of paragraph 1 or 2 comprises an amino acid substitution at a position selected from the group consisting of T40, F263, S288 and Y364 corresponding to the amino acid sequence of SEQ ID NO: 1.

4. In some embodiments of the variant α-amylase of paragraph 3, the variant comprises an amino acid substitution selected from the group consisting of T40C, T40D, T40E, T40N, F263P, F263Y, S288D, S288K, Y364E, Y364L and Y364M corresponding to the amino acid sequence of SEQ ID NO: 1.

5. In some embodiments, the variant α-amylase of any of paragraphs 1-4 further comprises:
(i) a deletion or substitution at one or more residues corresponding to positions 181, 182, 183 and/or 184 in the amino acid sequence of SEQ ID NO: 1;
(ii) a deletion of residues 181 and 182 or 183 and 184 corresponding to positions 181, 182, 183 and/or 184 in the amino acid sequence of SEQ ID NO: 1;
(iii) any single, multiple or combinatorial mutation(s) previously described in a Family 13 α-amylase; and/or
(iv) an N-terminal and/or C-terminal truncation.

6. In some embodiments, the variant α-amylase of any of paragraphs 1-5, has at least 70%, at least 80%, at least 90% or at least 95% amino acid sequence identity to the amino acid sequence of SEQ ID NO: 1; encoded by a polynucleotide having at least 60%, at least 70%, at least 80% or at least 90% nucleic acid sequence identity to a polynucleotide encoding SEQ ID NO: 1; and/or encoded by a polynucleotide that hybridizes under stringent conditions to a polynucleotide encoding SEQ ID NO: 1, or the complement, thereof.

7. In another aspect, a method for modulating the activity of an α-amylase is provided, comprising introducing into a parental Family 13 α-amylase having at least 60% amino acid sequence identity to the amino acid sequence of SEQ ID NO: 1 a mutation of a residue that affects the electrostatic environment of the general acid positioned for catalysis, wherein the mutation is located at the N-terminal side of the α-amylase β-barrel, and wherein the mutation changes the electrostatic environment of the general acid in the resulting variant α-amylase.

8. In some embodiments of the method of paragraph 7, the ratio of the activity of the variant α-amylase at pH 8.5 compared to the activity at pH 10.5 divided by the ratio

3 of the activity at pH 8.5 compared to the activity at pH 10.5 of an otherwise identical α-amylase lacking the amino acid mutation in an amino acid residue that lines the N-terminal side of the core β-barrel structure of the α-amylase is greater than 1, greater than 2, greater than 3, or greater than 4.

9. In some embodiments of the method of paragraph 7 or 8, the mutation is a substitution at a position selected from the group consisting of T40, F263, S288 and Y364 corresponding to the amino acid sequence of SEQ ID NO: 1.

10. In some embodiments of the method of paragraph 9, the substitution is selected from the group consisting of T40C, T40D, T40E, T40N, F263P, F263Y, S288D, S288K, Y364E, Y364L and Y364M corresponding to the amino acid sequence of SEQ ID NO: 1.

11. In some embodiments of the method of any of paragraphs 7-10, the variant α-amylase further comprises:

(i) a deletion or substitution at one or more residues corresponding to positions 181, 182, 183 and/or 184 in the amino acid sequence of SEQ ID NO: 1;

(ii) a deletion of residues 181 and 182 or 183 and 184 corresponding to positions 181, 182, 183 and/or 184 in the amino acid sequence of SEQ ID NO: 1;

(iii) any single, multiple or combinatorial mutation(s) previously described in a Family 13 α-amylase; and/or (iv) an N-terminal and/or C-terminal truncation.

12. In another aspect, a composition for liquefying starch comprising the variant α-amylase of any of paragraphs 1-6 is provided.

13. In another aspect, a detergent composition comprising the variant amylase of any of paragraphs 1-6 is provided.

14. In another aspect, a method for converting starch to oligosaccharides is provided, comprising contacting starch with effective amount of the variant amylase of any of paragraphs 1-6.

15. In another aspect, a method for removing a starchy stain or soil from a surface is provided, comprising contacting the surface with an effective amount of the variant amylase of any of paragraphs 1-6, and allowing the polypeptide to hydrolyze starch components present in the starchy stain to produce smaller starch-derived molecules that dissolve in the aqueous composition, thereby removing the starchy stain from the surface.

These and other aspects and embodiments of the compositions and methods will be apparent from the present description and drawings.

BRIEF DESCRIPTION OF THE DRAWINGS

FIG. 1 is an amino acid sequence alignment of BspAmy24, Amy707 and AA560.

4

Figure 7:
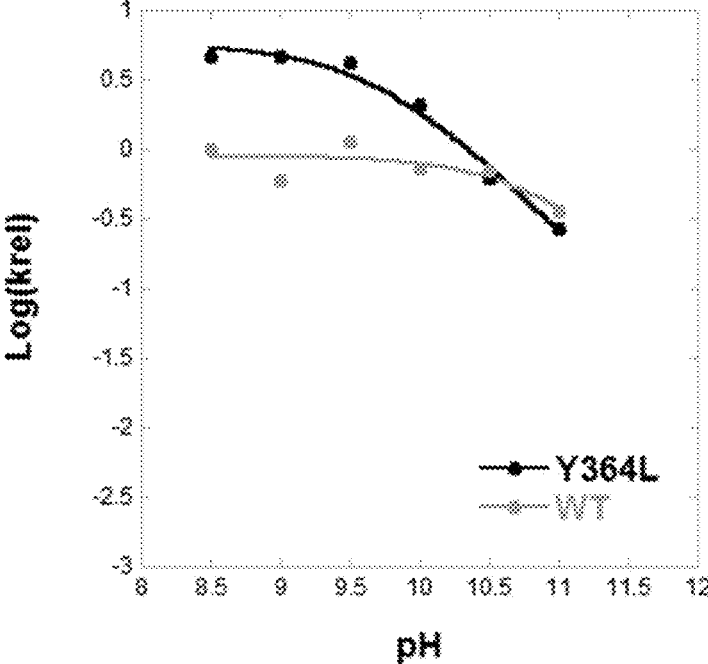

FIG. 7 is a plot of the log of rate constant versus pH for BspAmy24-V1 and BspAmy24-V1-Y364L.

DETAILED DESCRIPTION

Described are compositions and methods relating to variant α-amylase enzymes. Exemplary applications for the variant amylase enzymes are for starch liquefaction and saccharification, for cleaning starchy stains in laundry, dishwashing, and other applications, for textile processing (e.g., desizing), in animal feed for improving digestibility, and for baking and brewing. These and other aspects of the compositions and methods are described in detail, below.

Prior to describing the various aspects and embodiments of the present compositions and methods, the following definitions and abbreviations are described.

1. Definitions and Abbreviations

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art. The following terms are defined, below, for clarity.

1.1. Abbreviations and Acronyms

The following abbreviations/acronyms have the following meanings unless otherwise specified:

DNA deoxyribonucleic acid
EC Enzyme Commission
GA glucoamylase
GH general hardness
HDL high density liquid detergent
HDD heavy duty powder detergent
HSG high suds granular detergent
HFCS high fructose corn syrup
IRS insoluble residual starch
kDa kiloDalton
MW molecular weight
MWU modified Wohlgemuth unit; $1.6 \times 10^{-5}$ mg/MWU=unit of activity
NCBI National Center for Biotechnology Information
PI performance index
ppm parts per million, e.g., μg protein per gram dry solid
RCF relative centrifugal/centripetal force (i.e., x gravity)
sp. species
w/v weight/volume
w/w weight/weight
v/v volume/volume
wt % weight percent
° C. degrees Centigrade
$H_2O$ water
$dH_2O$ or DI deionized water dIH$_2$O deionized water, Milli-Q filtration
g or gm grams
micrograms
mg milligrams
kg kilograms
μL and μl microliters
mL and ml milliliters
mm millimeters
μm micrometer
M molar
mM millimolar
micromolar
U units
sec seconds
min(s) minute/minutes
hr(s) hour/hours
ETOH ethanol
N normal
MWCO molecular weight cut-off
CAZy Carbohydrate-Active Enzymes database
WT wild-type

1.2. Definitions

The terms "amylase" or "amylolytic enzyme" refer to an enzyme that is, among other things, capable of catalyzing the degradation of starch. α-amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) O-glycosidic linkages within the starch molecule in a random fashion yielding polysaccharides containing three or more (1-4)-α-linked D-glucose units. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the polysaccharide molecule from the non-reducing end of the substrate. β-amylases, α-glucosidases (EC 3.2.1.20; α-D-glucoside glucohydrolase), glucoamylase (EC 3.2.1.3; α-D-(1→4)-glucan glucohydrolase), and product-specific amylases like the maltotetraosidases (EC 3.2.1.60) and the maltohexaosidases (EC 3.2.1.98) can produce malto-oligosaccharides of a specific length or enriched syrups of specific maltooligosaccharides.

The term "starch" refers to any material comprised of the complex polysaccharide carbohydrates of plants, comprised of amylose and amylopectin with the formula (C$_6$H$_{10}$O$_5$)$_x$, wherein X can be any number. The term includes plant-based materials such as grains, cereal, grasses, tubers and roots, and more specifically materials obtained from wheat, barley, corn, rye, rice, sorghum, brans, cassava, millet, milo, potato, sweet potato, and tapioca. The term "starch" includes granular starch. The term "granular starch" refers to raw, i.e., uncooked starch, e.g., starch that has not been subject to gelatinization.

As used herein, the term "liquefaction" or "liquefy" means a process by which starch is converted to less viscous and shorter chain dextrins.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

Reference to the wild-type polypeptide is understood to include the mature form of the polypeptide. A "mature" polypeptide or variant, thereof, is one in which a signal sequence is absent, for example, cleaved from an immature form of the polypeptide during or following expression of the polypeptide.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

In the case of the present α-amylases, "activity" refers to α-amylase activity, which can be measured as described herein.

The expression "core β-barrel structure" refers to the amino acid residues that form a central region of parallel β-sheet secondary structure, curving upon itself such that the first strand hydrogen bonds with the last strand in a continuous barrel. In particular, in BspAmy24, the amino acids that form the barrel are residues 8-11, 40-44, 98-103, 232-235, 263-267, 288-290, 325-328, 364-368.

The expression "an amino acid residue that lines the N-terminal side of the core β-barrel structure" refers to an amino acid at the end of the core β-barrel structure that is opposite to the side that is adjacent to the active site. The strands that comprise the barrel are oriented in parallel, such that the N-terminal ends of the β strands lie on one side of the barrel and the C-terminal ends of the strands lie on the other side of the barrel, adjacent to the active site. More specifically, the amino acids that line the N-terminal side of the core β-barrel include the most N-terminal residues of each strand that are engaged in hydrogen bonding with adjacent strands, as defined by common algorithms to assign secondary structure such as in PyMol and MOE, as well as the residue immediately before or after those residues if engaged in backbone hydrogen bonding with an adjacent strand. In particular, the residues that line the N-terminal side of the core β-barrel structure in BspAmy24 include positions 8, 9, 40, 41, 97, 98, 230, 232, 263, 288, 325, 326, 364.

The apparent pK$_a$ of the general acid refers to the experimentally determined value for the higher pK$_a$ of the enzyme's activity, such that at pH values above the pK$_a$, the activity decreases with increasing pH, with a roughly one order of magnitude drop in activity for each pH unit at values well above the pK$_a$. This observed pK$_a$ is expected to correspond to that of the general acid in the reaction mechanism (Rydberg, E. H. et al. (2002) Mechanistic analyses of catalysis in human pancreatic α-amylases: Detailed kinetic and structural studies of three conserved carboxylic acids. *Biochemistry* 41:4492-4502), yet it is also acknowledged that kinetic properties of the enzyme and other ionizations may complicate the direct assignment.

The term "performance benefit" refers to an improvement in a desirable property of a molecule. Exemplary performance benefits include, but are not limited to, increased hydrolysis of a starch substrate, increased grain, cereal or other starch substrate liquefaction performance, increased cleaning performance, increased thermal stability, increased detergent stability, increased storage stability, increased solubility, an altered pH profile, decreased calcium dependence, increased specific activity, modified substrate specificity, modified substrate binding, modified pH-dependent activity, modified pH-dependent stability, increased oxidative stability, and increased expression. In some cases, the performance benefit is realized at a relatively low temperature. In some cases, the performance benefit is realized at relatively high temperature.

The terms "combinatorial variants" are variants comprising two or more mutations, e.g., 2, 3, 4, 5, 6, 7, 8, 9, 10, or more, substitutions, deletions, and/or insertions.

The term "recombinant," when used in reference to a subject cell, nucleic acid, protein or vector, indicates that the subject has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding an amylase is a recombinant vector.

The terms "recovered," "isolated," and "separated," refer to a compound, protein (polypeptides), cell, nucleic acid, amino acid, or other specified material or component that is removed from at least one other material or component with which it is naturally associated as found in nature. An "isolated" polypeptide, thereof, includes, but is not limited to, a culture broth containing secreted polypeptide expressed in a heterologous host cell.

The term "purified" refers to material (e.g., an isolated polypeptide or polynucleotide) that is in a relatively pure state, e.g., at least about 90% pure, at least about 95% pure, at least about 98% pure, or even at least about 99% pure.

The term "enriched" refers to material (e.g., an isolated polypeptide or polynucleotide) that is in about 50% pure, at least about 60% pure, at least about 70% pure, or even at least about 70% pure.

The terms "thermostable" and "thermostability," with reference to an enzyme, refer to the ability of the enzyme to retain activity after exposure to an elevated temperature. The thermostability of an enzyme, such as an amylase enzyme, is measured by its half-life ($t_{1/2}$) given in minutes, hours, or days, during which half the enzyme activity is lost under defined conditions. The half-life may be calculated by measuring residual α-amylase activity following exposure to (i.e., challenge by) an elevated temperature.

A "pH range," with reference to an enzyme, refers to the range of pH values under which the enzyme exhibits catalytic activity.

The terms "pH stable" and "pH stability," with reference to an enzyme, relate to the ability of the enzyme to retain activity over a wide range of pH values for a predetermined period of time (e.g., 15 min., 30 min., 1 hour).

The term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may contain chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

"Hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1×SSC=0.15 M NaCl, 0.015 M Na3 citrate, pH 7.0). Hybridized, duplex nucleic acids are characterized by a melting temperature (Tm), where one half of the hybridized nucleic acids are unpaired with the complementary strand.

A "synthetic" molecule is produced by in vitro chemical or enzymatic synthesis rather than by an organism.

The terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., an amylase) has been introduced. Exemplary host strains are microorganism cells (e.g., bacteria, filamentous fungi, and yeast) capable of expressing the polypeptide of interest and/or fermenting saccharides. The term "host cell" includes protoplasts created from cells.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

The term "expression" refers to the process by which a polypeptide is produced based on a nucleic acid sequence. The process includes both transcription and translation.

The term "specific activity" refers to the number of moles of substrate that can be converted to product by an enzyme or enzyme preparation per unit time under specific conditions. Specific activity is generally expressed as units (U)/ mg of protein.

As used herein, "water hardness" is a measure of the minerals (e.g., calcium and magnesium) present in water.

A "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

A "smaller swatch" or "micro swatch" is a section of the swatch that has been cut with a single hole punch device, or has been cut with a custom manufactured multiple-hole punch device, where the pattern of the multi-hole punch is matched to standard multi-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The smaller swatch can also be made by applying a stain to a small piece of material. For example, the smaller swatch can be a stained piece of fabric ⅝" or 0.25" or 5.5 mm in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of metal, plastic, glass, ceramic, or another suitable material that is coated with the soil substrate. The one or more coated beads are then placed into wells of 96-, 48-, or 24-well plates or larger formats, containing suitable buffer and enzyme. In other conceivable methods, the stained fabric is exposed to enzyme by spotting enzyme solution onto the fabric, by wetting swatch attached to a holding device, or by immersing the swatch into a larger solution containing enzyme.

"A cultured cell material comprising an amylase" or similar language, refers to a cell lysate or supernatant (including media) that includes an amylase as a component. The cell material may be from a heterologous host that is grown in culture for the purpose of producing the amylase.

"Percent sequence identity" means that a particular sequence has at least a certain percentage of amino acid residues identical to those in a specified reference sequence, when aligned using the CLUSTAL W algorithm with default parameters. See Thompson et al. (1994) Nucleic Acids Res. 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF Percent identity for multiple sequence can also be determined using MUSCLE (Edgar, R. C. (2004) Nuc. Acids Res. 32:1792-97 and Edgar, R. C. (2004) Bioinformatics 5:113). In all cases, deletions are counted as non-identical residues, compared to a reference sequence.

"Fused" polypeptide sequences are connected, i.e., operably linked, via a peptide bond between two subject polypeptide sequences.

The term "filamentous fungi" refers to all filamentous forms of the subdivision Eumycotina, particularly Pezizomycotina species.

The term "dry solids content" (ds) refers to the total solids of a slurry in a dry weight percent basis. The term "slurry" refers to an aqueous mixture containing insoluble solids.

The phrase "simultaneous saccharification and fermentation (SSF)" refers to a process in the production of bio-chemicals in which a microbial organism, such as an ethanologenic microorganism, and at least one enzyme, such as an amylase, are present during the same process step. SSF includes the contemporaneous hydrolysis of starch substrates (granular, liquefied, or solubilized) to saccharides, including glucose, and the fermentation of the saccharides into alcohol or other biochemical or biomaterial in the same reactor vessel.

An "ethanologenic microorganism" refers to a microorganism with the ability to convert a sugar or oligosaccharide to ethanol.

The term "fermented beverage" refers to any beverage produced by a method comprising a fermentation process, such as a microbial fermentation, e.g., a bacterial and/or fungal fermentation. "Beer" is an example of such a fermented beverage, and the term "beer" is meant to comprise any fermented wort produced by fermentation/brewing of a starch-containing plant material. Often, beer is produced exclusively from malt or adjunct, or any combination of malt and adjunct.

The term "malt" refers to any malted cereal grain, such as malted barley or wheat.

The term "adjunct" refers to any starch and/or sugar containing plant material that is not malt, such as barley or wheat malt. Examples of adjuncts include common corn grits, refined corn grits, brewer's milled yeast, rice, sorghum, refined corn starch, barley, barley starch, dehusked barley, wheat, wheat starch, torrefied cereal, cereal flakes, rye, oats, potato, tapioca, cassava and syrups, such as corn syrup, sugar cane syrup, inverted sugar syrup, barley and/or wheat syrups, and the like.

The term "mash" refers to an aqueous slurry of any starch and/or sugar containing plant material, such as grist, e.g., comprising crushed barley malt, crushed barley, and/or other adjunct or a combination thereof, mixed with water later to be separated into wort and spent grains.

The term "wort" refers to the unfermented liquor run-off following extracting the grist during mashing.

The term "about" refers to ±15% to the referenced value.

2. Aspects and Embodiments of the Present Compositions and Methods

The following paragraphs describe in detail various aspects and embodiments of the present compositions and methods.

2.1. α-Amylase Variants Having a Reduced pKa of their General Acid

One way to increase the activity of an α-amylase is to reduce the $pK_a$ of its general acid. Lowering the $pK_a$ of a general acid results in an increase in reactivity of the protonated species. The Brønsted equation for the reactivity of a general acid (see, e.g., Jencks, W. P. (1986) Catalysis in Chemistry and Enzymology, Dover Publications, New York) expresses the relationship between $pK_a$ and reactivity with a factor "α" that is characteristic of a given reaction, where $k_{HA}$ is the rate constant of the protonated species, $pK_a$ is the $pK_a$ of that general acid, and C is a constant:

$$\log(k_{HA}) = -\alpha(pK_a) + C$$

While it is well established that reducing the $pK_a$ of a general acid can increase the reactivity of the fully protonated species, the means and mechanisms of shifting the $pK_a$ of an amino acid side chain acting as a general acid within an enzyme active site are often highly complex. Effects such as nearby charged or hydrophobic environments can alter pK$_a$ values (see, e.g., Schmidt, D. E. and Westheimer, F. H. (1971) pK of the lysine amino group at the active site of acetoacetate decarboxylase. *Biochemistry* 10:1249-53 and Ho, M C. et al. (2009) The origin of the electrostatic perturbation in acetoacetate decarboxylase. *Nature* 459:393-97). In general, it is difficult to predict the impact of protein mutations on pK$_a$ values for catalytic side chains in all enzymes, including α-amylases (Nielsen, J. E. and Borchert, T. V. (2000) Protein engineering of bacterial α-amylases. *Biochimica et Biophysica Acta* 1543:253-274).

Figure 2:
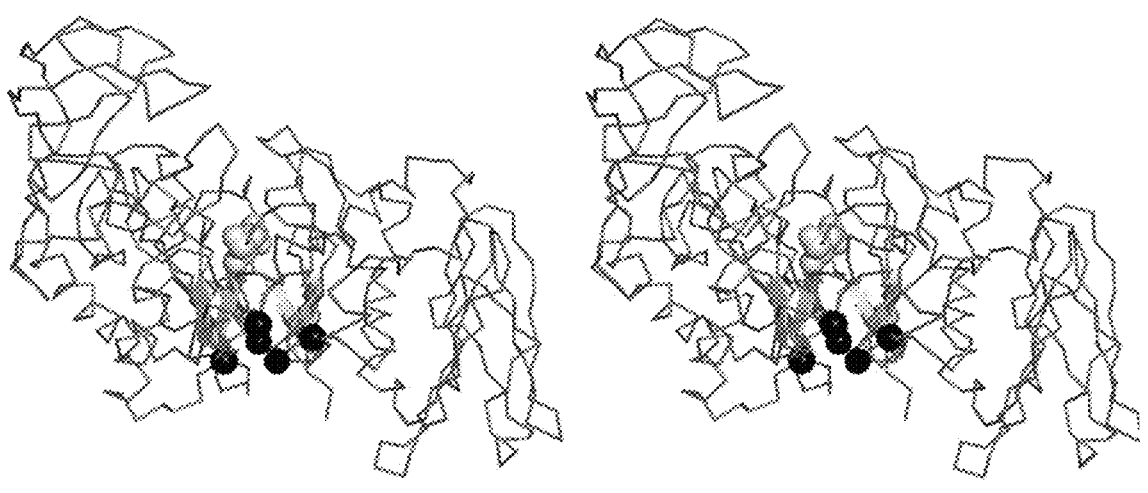
FIG. 2 shows a structural model of BspAmy24 (del-R181-G182) for viewing with conventional stereo viewer.
Figure 3:
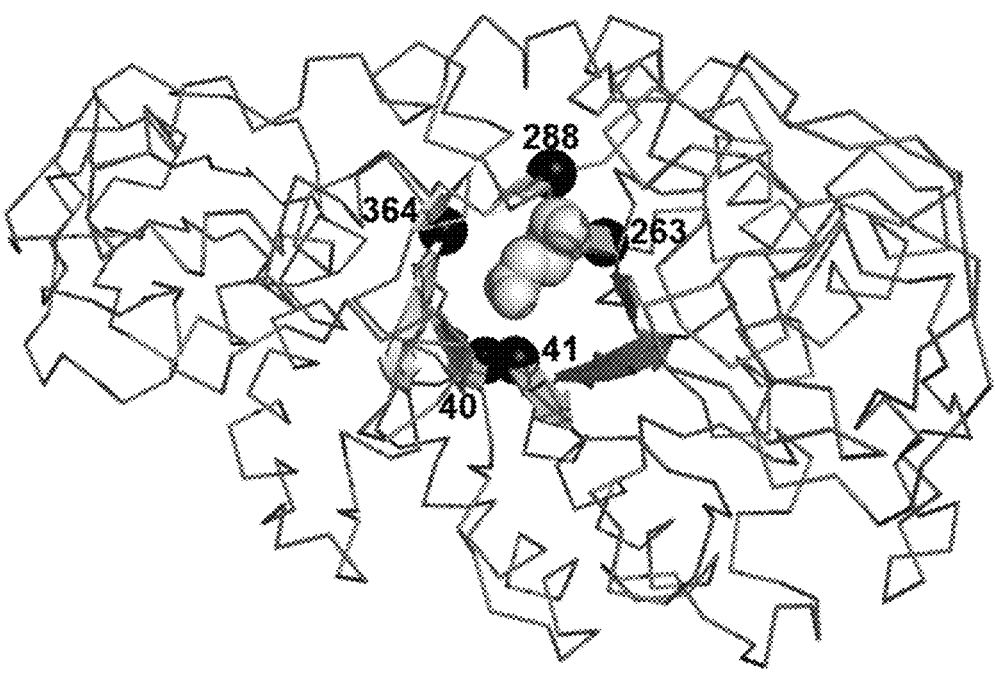
FIG. 3 shows the structural model of BspAmy24 (del-R181-G182) from a different angle. The α carbon positions are shown in black for residues 40, 41, 263, 288, and 364. The general acid residues are shown as gray spheres.
Figure 4:
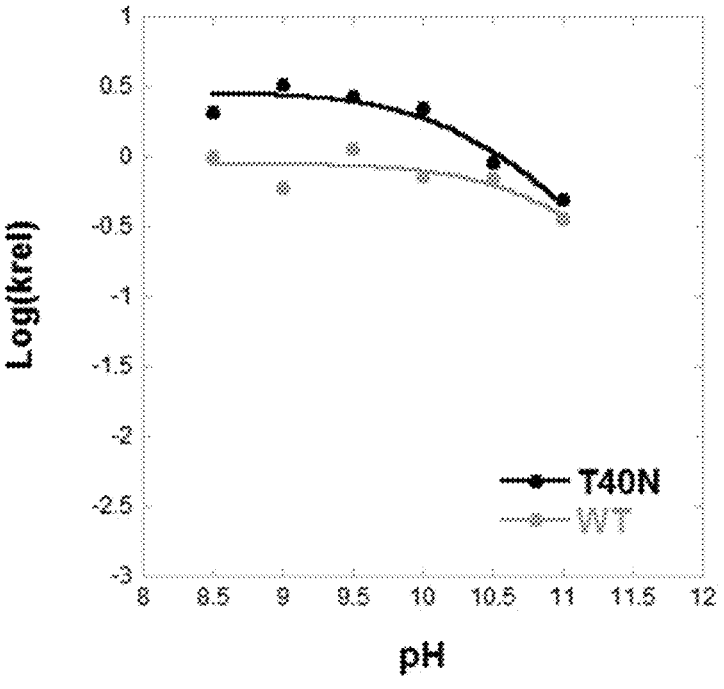
FIG. 4 is a plot of the log of rate constant versus pH for BspAmy24-V1 and BspAmy24-V1-T240N.
Figure 5:
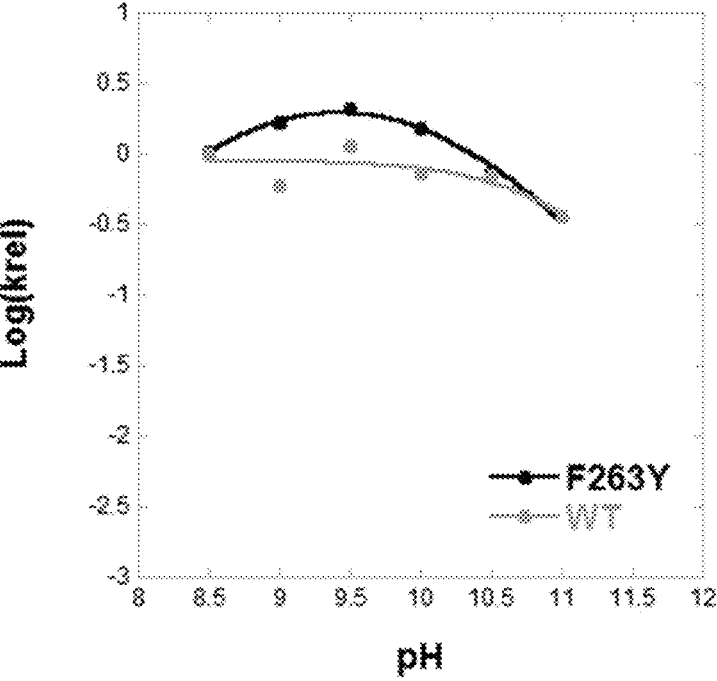
FIG. 5 is a plot of the log of rate constant versus pH for BspAmy24-V1 and BspAmy24-V1-F263Y.
Figure 6:
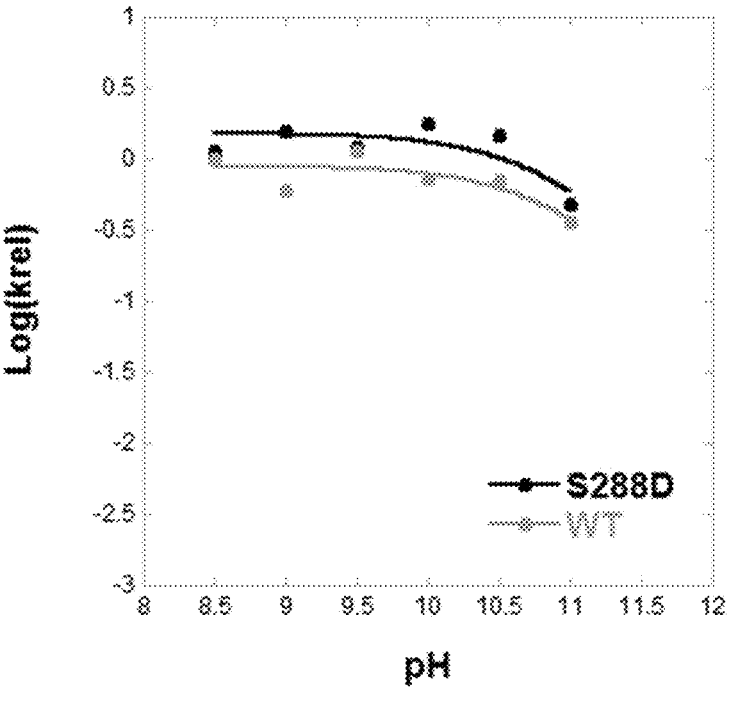
FIG. 6 is a plot of the log of rate constant versus pH for BspAmy24-V1 and BspAmy24-V1-S288D.

As described, herein, a set of residues that line the N-terminal side of the core β-barrel in a α-amylases were unexpectedly found to substantially impact the measured enzyme pK$_a$ values and to increase the activity of the α-amylases at pH values near and below the pK$_a$. The positions of these residues are shown in FIGS. 2 and 3. Mutations of these amino acids resulted in reduction of the pK$_a$ value that is expected to correspond to that of the general acid in the reaction (Rydberg, E. H. et al. (2002) Mechanistic analyses of catalysis in human pancreatic α-amylases: Detailed kinetic and structural studies of three conserved carboxylic acids. *Biochemistry* 41:4492-4502).

Without being limited to a theory, it is posulated that mutation of these residues may impact the electrostatic environment of the general acid because their interactions anchor the barrel in which the general acid is positioned for catalysis. Alternative packing arrangements at the N-terminal side of the barrel may serve to tighten or loosen the barrel and thus change the electrostatic environment of the general acid.

The model α-amylase used to exemplify the present compositions and methods is an α-amylase from a *Bacillus* sp., herein referred to as "BspAmy24." The amino acid sequence of BspAmy24 α-amylase is shown, below, as SEQ ID NO: 1:

```
HHNGTNGTMM QYFEWHLPND GQHWNRLRND AANLKNLGIT

AVWIPPAWKG TSQNDVGYGA YDLYDLGEFN QKGTIRTKYG

TRSQLQSAIA SLQNNGIQVY GDVVMNHKGG ADGTEWVQAV

EVNPSNRNQE VTGEYTIEAW TKFDFPGRGN THSSFKWRWY

HFDGTDWDQS RQLNNRIYKF RGTGKAWDWE VDTENGNYDY

LMYADVDMDH PEVINELRRW GVWYTNTLNL DGFRIDAVKH

IKYSFTRDWL NHVRSTTGKN NMFAVAEFWK NDLGAIENYL

HKTNWNHSVF DVPLHYNLYN ASKSGGNYDM RQILNGTVVS

KHPIHAVTFV DNHDSQPAEA LESEVEAWFK PLAYALILTR

EQGYPSVFYG DYYGIPTHGV AAMKGKIDPI LEARQKYAYG

TQHDYLDHHN IIGWTREGNS AHPNSGLATI MSDGPGGSKW

MYVGRHKAGQ VWRDITGNRT GTVTINADGW GNFSVNGGSV

SIWVNK
```

BspAmy24 is similar to an α-amylase from a *Bacillus* sp. 707 that is referred to as "Amy707" α-amylase. The amino acid sequence of Amy707 α-amylase is shown, below, as SEQ ID NO: 2:

```
HHNGTNGTMM QYFEWYLPND GNHWNRLNSD ASNLKSKGIT

AVWIPPAWKG ASQNDVGYGA YDLYDLGEFN QKGTVRTKYG

TRSQLQAAVT SLKNNGIQVY GDVVMNHKGG ADATEMVRAV

EVNPNNRNQE VTGEYTIEAW TRFDFPGRGN THSSFKWRWY

HFDGVDWDQS RRLNNRIYKF RGHGKAWDWE VDTENGNYDY

LMYADIDMDH PEVVNELRNW GVWYTNTLGL DGFRIDAVKH

IKYSFTRDWI NHVRSATGKN MFAVAEFWKN DLGAIENYLQ

KTNWNHSVFD VPLHYNLYNA SKSGGNYDMR NIFNGTVVQR

HPSHAVTFVD NHDSQPEEAL ESFVEEWFKP LAYALTLTRE

QGYPSVFYGD YYGIPTHGVP AMRSKIDPIL EARQKYAYGK

QNDYLDHHNI IGWTREGNTA HPNSGLATIM SDGAGGSKWM

FVGRNKAGQV WSDITGNRTG TVTINADGWG NFSVNGGSVS

IWVNK
```

BspAmy24 is also similar to an α-amylase from another *Bacillus* sp. that is referred to as AA560 α-amylase, having an amino acid sequence as shown below, as SEQ ID NO: 3:

```
HHNGTNGTMM QYFEWYLPND GNHWNRLRSD ASNLKDKGIS

AVWIPPAWKG ASQNDVGYGA YDLYDLGEFN QKGTIRTKYG

TRNQLQAAVN ALKSNGIQVY GDVVMNHKGG ADATEMVRAV

EVNPNNRNQE VSGEYTIEAW TKFDFPGRGN THSNFKWRWY

HFDGVDWDQS RKLNNRIYKF RGDGKGWDWE VDTENGNYDY

LMYADIDMDH PEVVNELRNW GVWYTNTLGL DGFRIDAVKH

IKYSFTRDWI NHVRSATGKN MFAVAEFWKN DLGAIENYLN

KTNWNHSVFD VPLHYNLYNA SKSGGNYDMR QIFNGTVVQR

HPMHAVTFVD NHDSQPEEAL ESFVEEWFKP LAYALTLTRE

QGYPSVFYGD YYGIPTHGVP AMKSKIDPIL EARQKYAYGR

QNDYLDHHNI IGWTREGNTA HPNSGLATIM SDGAGGNKWM

FVGRNKAGQV WTDITGNRAG TVTINADGWG NFSVNGGSVS

IWVNK
```

An amino acid sequence alignment of BspAmy24, Amy707 and AA560 is shown in FIG. 1. An amino acid sequence identity matrix using MUSCLE is shown in Table 1.

TABLE 1

| Amino acid sequence identity matrix of BspAmy24, Amy707 and AA560 | | | |
|---|---|---|---|
| | BspAmy24 | Amy707 | AA560 |
| BspAmy24 | (100) | 90.3 | 89.5 |
| Amy707 | 90.3 | (100) | 95.5 |
| AA560 | 89.5 | 95.5 | (100) |

In some embodiments, the variant α-amylase has at least 60%, at least 70%, at least 80%, at least 85%, at least 89%, at least 90%, at least 91%, at least 92%, at least 93%, at least 94%, at least 95%, at least 96%, at least 97%, at least 98%, or even at least 99% amino acid sequence identity to SEQ ID NO: 1, 2 and/or 3, excluding the wild-type BspAmy24, Amy707 and AA560, and known variants, thereof.

It is known that many bacterial (and other) α-amylases share the same fold, and often benefit from the same mutations. In the present case, corresponding amino acid positions in other α-amylases can readily be identified by amino acid sequence alignment with BspAmy24, Amy707 and AA560 using Clustal W with default parameters. α-amylases in which the foregoing mutations are likely to produce a performance benefit include those having a similar fold and/or having 60% or greater amino acid sequence identity to any of the well-known *Bacillus* amylases (e.g., from *B. licheniformis, B. stearothermophilus, B. amyloliquifaciens, Bacillus* sp. SP722, *Cytophaga* sp. and the like), Carbohydrate-Active Enzymes database (CAZy) Family 13 amylases, or any amylase that has heretofore been referred to by the descriptive term, "Termamyl-like." The reader will appreciate that where an α-amylase naturally has a mutation listed above (i.e., where the wild-type α-amylase already comprised a residue identified as a mutation), then that particular mutation does not apply to that α-amylase. However, other described mutations may work in combination with the naturally occurring residue at that position. Because of their close sequence identity, mutations (including substitutions, insertions, and deletions, that produce a beneficial effect in BspAmy24 are particularly likely to produce a similar effect in Amy707 and AA560 α-amylase, and vice versa.

2.2 Additional Mutations

In some embodiments, in addition to one or more of the mutations described above (e.g., in Section 2.1), the present amylases further include one or more mutations that provide a further performance or stability benefit. Exemplary performance benefits include but are not limited to increased hydrolysis of a starch substrate, increased grain, cereal or other starch substrate liquefaction performance, increased cleaning performance, increased thermal stability, increased storage stability, increased solubility, an altered pH profile, decreased calcium dependence, increased specific activity, modified substrate specificity, modified substrate binding, modified pH-dependent activity, modified pH-dependent stability, increased oxidative stability, and increased expression. In some cases, the performance benefit is realized at a relatively low temperature. In some cases, the performance benefit is realized at relatively high temperature.

In some embodiments, the present α-amylase variants additionally have at least one mutation in the calcium binding loop based on the work of Suzuki et al. (1989) J. Biol. Chem. 264:18933-938. Exemplary mutations include a deletion or substitution at one or more residues corresponding to positions 181, 182, 183 and/or 184 in any of SEQ ID NOs: 1-3. In particular embodiments, the mutation corresponds to the deletion of 181 and 182 or 183 and 184 (using any of SEQ ID NOs: 1-3 for numbering). Homologous residues in other amylases can be determined by structural alignment, or by primary structure alignment.

In some embodiments, the present α-amylase variants additionally have at least one mutation known to produce a performance, stability, or solubility benefit in other microbial α-amylases, including but not limited to those having a similar fold and/or having 60% or greater amino acid sequence identity to any of SEQ ID NOs: 1-3, Carbohydrate-Active Enzymes database (CAZy) Family 13 amylases, or any amylase that has heretofore been referred to by the descriptive term, "Termamyl-like." Amino acid sequence identity can be determined using Clustal W with default parameters.

The present amylases may include any number of conservative amino acid substitutions. Exemplary conservative amino acid substitutions are listed in Table 2.

TABLE 2

| Conservative amino acid substitutions | | |
|---|---|---|
| Amino Acid | Code | Replace with any of: |
| Alanine | A | D-Ala, Gly, β-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

It will be appreciated that some of the above mentioned conservative mutations can be produced by genetic manipulation, while others are produced by introducing synthetic amino acids into a polypeptide by genetic or other means.

The present amylase may also be derived from any of the above-described amylase variants by substitution, deletion or addition of one or several amino acids in the amino acid sequence, for example less than 10, less than 9, less than 8, less than 7, less than 6, less than 5, less than 4, less than 3, or even less than 2 substitutions, deletions or additions. Such variants should have the same activity as amylase from which they were derived. Particular deletions include N-terminal and/or C-terminal truncations of one or a few amino acid residues, for example, 1, 2, 3, 4, or 5 amino acid residues.

The present amylase may be "precursor," "immature," or "full-length," in which case they include a signal sequence, or "mature," in which case they lack a signal sequence. Mature forms of the polypeptides are generally the most useful. Unless otherwise noted, the amino acid residue numbering used herein refers to the mature forms of the respective amylase polypeptides. The present amylase polypeptides may also be truncated to remove the N or C-termini, so long as the resulting polypeptides retain amylase activity.

The present amylase may be a "chimeric," "hybrid" or "domain swap" polypeptide, in that it includes at least a portion of a first amylase polypeptide, and at least a portion of a second amylase polypeptide. The present amylases may further include heterologous signal sequence, an epitope to allow tracking or purification, or the like. Exemplary heter- 15
16 ologous signal sequences are from *B. licheniformis* amylase (LAT), *B. subtilis* (AmyE or AprE), and *Streptomyces* CelA.

2.3. Nucleotides Encoding Variant Amylase Polypeptides

In another aspect, nucleic acids encoding a variant amylase polypeptide are provided. The nucleic acid may encode a particular amylase polypeptide, or an amylase having a specified degree of amino acid sequence identity to the particular amylase.

In some embodiments, the nucleic acid encodes an amylase having at least 90%, at least 91%, at least 92%, at least 93%, at least 94%, at least 95%, at least 96%, at least 97%, at least 98%, or even at least 99% amino acid sequence identity to one or more of SEQ ID NOs: 1-3. It will be appreciated that due to the degeneracy of the genetic code, a plurality of nucleic acids may encode the same polypeptide.

3. Production of Variant Amylases

The present variant amylases can be produced in host cells, for example, by secretion or intracellular expression, using methods well-known in the art. Fermentation, separation, and concentration techniques are well known in the art and conventional methods can be used to prepare a concentrated, variant-α-amylase-polypeptide-containing solution.

For production scale recovery, variant α-amylase polypeptides can be enriched or partially purified as generally described above by removing cells via flocculation with polymers. Alternatively, the enzyme can be enriched or purified by microfiltration followed by concentration by ultrafiltration using available membranes and equipment. However, for some applications, the enzyme does not need to be enriched or purified, and whole broth culture can be lysed and used without further treatment. The enzyme can then be processed, for example, into granules.

4. Carbohydrate Processing Compositions and Uses of Variant Amylases

Variants amylases are useful for a variety of carbohydrate processing applications that are well-known in the art and are not reiterated, herein. These uses include fuel ethanol production, syrup production and the production of other valuable biochemicals.

4.1. Preparation of Starch Substrates

Methods for preparing starch substrates for use in the processes disclosed herein are well known. Useful starch substrates may be obtained from, e.g., tubers, roots, stems, legumes, cereals or whole grain. More specifically, the granular starch may be obtained from corn, cobs, wheat, barley, rye, triticale, milo, sago, millet, cassava, tapioca, sorghum, rice, peas, bean, banana, or potatoes. Specifically contemplated starch substrates are corn starch and wheat starch. The starch from a grain may be ground or whole and includes corn solids, such as kernels, bran and/or cobs. The starch may also be highly refined raw starch or feedstock from starch refinery processes.

4.2. Gelatinization and Liquefaction of Starch

Gelatinization is generally performed simultaneously with, or followed by, contacting a starch substrate with an α-amylase, although additional liquefaction-inducing enzymes optionally may be added. In some embodiments, the starch substrate prepared as described above is slurried with water. Liquefaction may also be performed at or below the liquefaction temperatures, as in a "cold cook" or "no cook process."

4.3. Saccharification

The liquefied starch can be saccharified into a syrup that is rich in lower DP (e.g., DP1+DP2) saccharides, using variant amylases, optionally in the presence of another enzyme(s). The exact composition of the products of saccharification depends on the combination of enzymes used, as well as the type of granular starch processed. Saccharification and fermentation may be performed simultaneously or in an overlapping manner (see, below).

4.4. Isomerization

The soluble starch hydrolysate produced by treatment with amylase can be converted into high fructose starch-based syrup (HFSS), such as high fructose corn syrup (HFCS). This conversion can be achieved using a glucose isomerase, particularly a glucose isomerase immobilized on a solid support.

4.5. Fermentation

The soluble starch hydrolysate, particularly a glucose rich syrup, can be fermented by contacting the starch hydrolysate with a fermenting organism. EOF products include metabolites, such as citric acid, lactic acid, succinic acid, monosodium glutamate, gluconic acid, sodium gluconate, calcium gluconate, potassium gluconate, itaconic acid and other carboxylic acids, glucono delta-lactone, sodium erythorbate, lysine and other amino acids, omega 3 fatty acid, butanol, isoprene, 1,3-propanediol and other biomaterials.

Ethanologenic microorganisms include yeast, such as *Saccharomyces cerevisiae* and bacteria, such as *Zymomonas moblis*, expressing alcohol dehydrogenase and pyruvate decarboxylase. Improved strains of ethanologenic microorganisms are known in the art. Commercial sources of yeast include ETHANOL RED® (LeSaffre); FERMAX™ (Martrex), THERMOSACC®, TRANSFERM® Yield+ and YP3™ (Lallemand); RED STAR® (Red Star); FERMIOL® (DSM Specialties); SUPERSTART® (Alltech); and SYNERXIA® and SYNERXIA® Thrive (DuPont Industrial Biosciences). Microorganisms that produce other metabolites, such as citric acid and lactic acid, by fermentation are also known in the art.

4.6. Compositions Comprising Variants Amylases and Additional Enzymes

Variant amylases may be combined with a glucoamylase (EC 3.2.1.3), from e.g., *Trichoderma, Aspergillus, Talaromyces, Clostridium, Fusarium, Thielavia, Thermomyces, Athelia, Humicola, Penicillium, Artomyces, Gloeophyllum, Pycnoporus, Steccherinum, Trametes* etc. Suitable commercial glucoamylases, include AMG 200L; AMG 300 L; SAN™ SUPER and AMG™ E (Novozymes); OPTIDEX® 300 and OPTIDEX L-400 (Danisco US Inc.); AMIGASE™ and AMIGASE™ PLUS (DSM); G-ZYME® G900 (Enzyme Bio-Systems); and G-ZYME® G990 ZR.

Other suitable enzymes that can be used with amylase include phytase, protease, pullulanase, β-amylase, isoamylase, α-glucosidase, cellulase, xylanase, other hemicellu-lases, β-glucosidase, transferase, pectinase, lipase, cutinase, esterase, mannanase, redox enzymes, a different α-amylase, or a combination thereof.

Compositions comprising the present amylases may be aqueous or non-aqueous formulations, granules, powders, gels, slurries, pastes, etc., which may further comprise any one or more of the additional enzymes listed, herein, along with buffers, salts, preservatives, water, co-solvents, surfac-tants, and the like. Such compositions may work in combi-nation with endogenous enzymes or other ingredients already present in a slurry, water bath, washing machine, food or drink product, etc., for example, endogenous plant (including algal) enzymes, residual enzymes from a prior processing step, and the like.

5. Compositions and Methods for Baking and Food Preparation

The present invention also relates to a "food composi-tion," including but not limited to a food product, animal feed and/or food/feed additives, comprising an amylase, and methods for preparing such a food composition comprising mixing variant amylase with one or more food ingredients, or uses thereof. Furthermore, the present invention relates to the use of an amylase in the preparation of a food compo-sition, wherein the food composition is baked subsequent to the addition of the polypeptide of the invention.

6. Brewing Compositions

The present variant amylase may be a component of a brewing composition used in a process of brewing, i.e., making a fermented malt beverage. Non-fermentable car-bohydrates form the majority of the dissolved solids in the final beer. This residue remains because of the inability of malt amylases to hydrolyze the alpha-1,6-linkages of the starch. The non-fermentable carbohydrates contribute about 50 calories per 12 ounces of beer. An amylase, in combi-nation with a glucoamylase and optionally a pullulanase and/or isoamylase, assists in converting the starch into dextrins and fermentable sugars, lowering the residual non-fermentable carbohydrates in the final beer.

7. Textile Desizing Compositions

Also contemplated are compositions and methods of treating fabrics (e.g., to desize a textile) using an amylase. Fabric-treating methods are well known in the art (see, e.g., U.S. Pat. No. 6,077,316). For example, the feel and appear-ance of a fabric can be improved by a method comprising contacting the fabric with an amylase in a solution. The fabric can be treated with the solution under pressure.

8. Cleaning Compositions

An aspect of the present compositions and methods is a cleaning composition that includes an amylase as a compo-nent. An amylase polypeptide can be used as a component in detergent compositions for, e.g., hand washing, laundry washing, dishwashing, and other hard-surface cleaning. Such compositions include heavy duty liquid (HDL), heavy duty dry (HDD), and hand (manual) laundry detergent compositions, including unit dose format laundry detergent compositions, and automatic dishwashing (ADW) and hand (manual) dishwashing compositions, including unit dose format dishwashing compositions.

8.1. Overview

An amylase polypeptide may be a component of a deter-gent composition, as the only enzyme or with other enzymes including other amylolytic enzymes. As such, it may be included in the detergent composition in the form of a non-dusting granulate, a stabilized liquid, or a protected enzyme.

The detergent composition may be in any useful form, e.g., as powders, granules, pastes, bars, or liquid. A liquid detergent may be aqueous, typically containing up to about 70% of water and 0% to about 30% of organic solvent. It may also be in the form of a compact gel type containing only about 30% water. The detergent composition comprises one or more surfactants, each of which may be anionic, nonionic, cationic, or zwitterionic. The detergent composi-tion may additionally comprise one or more other enzymes, such as proteases, another amylolytic enzyme, mannanase, cutinase, lipase, cellulase, pectate lyase, perhydrolase, xylanase, peroxidase, and/or laccase in any combination.

Particular forms of detergent compositions for inclusion of the present α-amylase are described, below. Many of these composition can be provided in unit dose format for ease of use. Unit dose formulations and packaging are described in, for example, US20090209445A1, US20100081598A1, U.S. Pat. No. 7,001,878B2, EP1504994B1, WO2001085888A2, WO2003089562A1, WO2009098659A1, WO2009098660A1, WO2009112992A1, WO2009124160A1, WO2009152031A1, WO2010059483A1, WO2010088112A1, WO2010090915A1, WO2010135238A1, WO2011094687A1, WO2011094690A1, WO2011127102A1, WO2011163428A1, WO2008000567A1, WO2006045391A1, WO2006007911A1, WO2012027404A1, EP1740690B1, WO2012059336A1, U.S. Pat. No. 6,730,646B1, WO2008087426A1, WO2010116139A1, and WO2012104613A1.

8.2. Heavy Duty Liquid (HDL) Laundry Detergent Composition

Exemplary HDL laundry detergent compositions includes a detersive surfactant (10%-40% wt/wt), including an anionic detersive surfactant (selected from a group of linear or branched or random chain, substituted or unsubstituted alkyl sulphates, alkyl sulphonates, alkyl alkoxylated sul-phate, alkyl phosphates, alkyl phosphonates, alkyl carboxy-lates, and/or mixtures thereof), and optionally non-ionic surfactant (selected from a group of linear or branched or random chain, substituted or unsubstituted alkyl alkoxylated alcohol, for example a C8-C18 alkyl ethoxylated alcohol and/or C6-C12 alkyl phenol alkoxylates), wherein the weight ratio of anionic detersive surfactant (with a hydro-philic index (HIc) of from 6.0 to 9) to non-ionic detersive surfactant is greater than 1:1. Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic sur-factants and mixtures thereof.

The composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkyleneimines in the range of 0.05 wt %-10 wt %) and/or random graft polymers (typically comprising of hydrophilic backbone comprising monomers selected from the group consisting of: unsaturated C1-C6 carboxylic acids, ethers, alcohols, aldehydes, ketones, esters, sugar units, alkoxy units, maleic anhydride, saturated polyalcohols such as glycerol, and mixtures thereof and hydrophobic side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof.

The composition may include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and copolymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition may further include saturated or unsaturated fatty acid, preferably saturated or unsaturated C12-C24 fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydoxyethyl cellulose, cationic starch, cationic polyacylamides, and mixtures thereof.

The composition may further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDTA), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition preferably included enzymes (generally about 0.01 wt % active enzyme to 0.03 wt % active enzyme) selected from proteases, amylases, lipases, cellulases, choline oxidases, peroxidases/oxidases, pectate lyases, mannanases, cutinases, laccases, phospholipases, lysophospholipases, acyltransferases, perhydrolases, arylesterases, and any mixture thereof. The composition may include an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition optionally includes silicone or fatty-acid based suds suppressors; hueing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof. The composition may be in any unit dose form, for example a pouch.

8.3. Heavy Duty Dry/Solid (HDD) Laundry Detergent Composition

Exemplary HDD laundry detergent compositions includes a detersive surfactant, including anionic detersive surfactants (e.g., linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (e.g., linear or branched or random chain, substituted or unsubstituted C8-C18 alkyl ethoxylates, and/or C6-C12 alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (e.g., alkanolamine sulpho-betaines), ampholytic surfactants, semi-polar non-ionic surfactants, and mixtures thereof; builders including phosphate free builders (for example zeolite builders examples which include zeolite A, zeolite X, zeolite P and zeolite MAP in the range of 0 wt % to less than 10 wt %), phosphate builders (for example sodium tri-polyphosphate in the range of 0 wt % to less than 10 wt %), citric acid, citrate salts and nitrilotriacetic acid, silicate salt (e.g., sodium or potassium silicate or sodium meta-silicate in the range of 0 wt % to less than 10 wt %, or layered silicate (SKS-6)); carbonate salt (e.g., sodium carbonate and/or sodium bicarbonate in the range of 0 wt % to less than 80 wt %); and bleaching agents including photobleaches (e.g., sulfonated zinc phthalocyanines, sulfonated aluminum phthalocyanines, xanthenes dyes, and mixtures thereof) hydrophobic or hydrophilic bleach activators (e.g., dodecanoyl oxybenzene sulfonate, decanoyl oxybenzene sulfonate, decanoyl oxybenzoic acid or salts thereof, 3,5,5- trimethy hexanoyl oxybenzene sulfonate, tetraacetyl ethylene diamine-TAED, nonanoyloxybenzene sulfonate-NOBS, nitrile quats, and mixtures thereof), sources of hydrogen peroxide (e.g., inorganic perhydrate salts examples of which include mono or tetra hydrate sodium salt of perborate, percarbonate, persulfate, perphosphate, or persilicate), preformed hydrophilic and/or hydrophobic peracids (e.g., percarboxylic acids and salts, percarbonic acids and salts, perimidic acids and salts, peroxymonosulfuric acids and salts, and mixtures thereof), and/or bleach catalysts (e.g., imine bleach boosters (examples of which include iminium cations and polyions), iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof, and metal-containing bleach catalysts (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid), and water-soluble salts thereof).

The composition preferably includes enzymes, e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and any mixture thereof.

The composition may optionally include additional detergent ingredients including perfume microcapsules, starch encapsulated perfume accord, hueing agents, additional polymers, including fabric integrity and cationic polymers, dye-lock ingredients, fabric-softening agents, brighteners (for example C.I. Fluorescent brighteners), flocculating agents, chelating agents, alkoxylated polyamines, fabric deposition aids, and/or cyclodextrin.

8.4. Automatic Dishwashing (ADW) Detergent Composition

Exemplary ADW detergent composition includes non-ionic surfactants, including ethoxylated non-ionic surfactants, alcohol alkoxylated surfactants, epoxy-capped poly (oxyalkylated) alcohols, or amine oxide surfactants present in amounts from 0 to 10% by weight; builders in the range of 5-60% including phosphate builders (e.g., mono-phosphates, di-phosphates, tri-polyphosphates, other oligomeric-poylphosphates, sodium tripolyphosphate-STPP) and phosphate-free builders (e.g., amino acid-based compounds including methyl-glycine-diacetic acid (MGDA) and salts and derivatives thereof, glutamic-N,N-diacetic acid (GLDA) and salts and derivatives thereof, iminodisuccinic acid (IDS) and salts and derivatives thereof, carboxy methyl inulin and salts and derivatives thereof, nitrilotriacetic acid (NTA), diethylene triamine penta acetic acid (DTPA), B-alaninediacetic acid (B-ADA) and their salts, homopolymers and copolymers of poly-carboxylic acids and their partially or completely neutralized salts, monomeric polycarboxylic acids and hydroxycarboxylic acids and their salts in the range of 0.5% to 50% by weight; sulfonated/carboxylated polymers in the range of about 0.1% to about 50% by weight to provide dimensional stability; drying aids in the range of about 0.1% to about 10% by weight (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds, thereof, particularly of the reactive cyclic carbonate and urea type); silicates in the range from about 1% to about 20% by weight (including sodium or potassium silicates for example sodium disilicate, sodium meta-silicate and crystalline phyllosilicates); inorganic bleach (e.g., perhydrate salts such as perborate, percarbonate, perphosphate, persulfate and persilicate salts) and organic bleach (e.g., organic peroxyacids, including diacyl and tetraacylperoxides, especially diperoxydodecanedioc acid, diperoxytetradecanedioc acid, and diperoxyhexadecanedioc acid); bleach activators (i.e., organic peracid precursors in the range from about 0.1% to about 10% by weight); bleach catalysts (e.g., manganese triazacyclononane and related complexes, Co, Cu, Mn, and Fe bispyridylamine and related complexes, and pentamine acetate cobalt(III) and related complexes); metal care agents in the range from about 0.1% to 5% by weight (e.g., benzatriazoles, metal salts and complexes, and/or silicates); enzymes in the range from about 0.01 to 5.0 mg of active enzyme per gram of automatic dishwashing detergent composition (e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and mixtures thereof); and enzyme stabilizer components (e.g., oligosaccharides, polysaccharides, and inorganic divalent metal salts).

8.5. Additional Enzymes

Any of the cleaning compositions described, herein, may include any number of additional enzymes. In general, the enzyme(s) should be compatible with the selected detergent, (e.g., with respect to pH-optimum, compatibility with other enzymatic and non-enzymatic ingredients, and the like), and the enzyme(s) should be present in effective amounts. The following enzymes are provided as examples.

Suitable proteases include those of animal, vegetable or microbial origin. Chemically modified or protein engineered mutants are included, as well as naturally processed proteins. The protease may be a serine protease or a metalloprotease, an alkaline microbial protease, a trypsin-like protease, or a chymotrypsin-like protease. Examples of alkaline proteases are subtilisins, especially those derived from *Bacillus*, e.g., subtilisin Novo, subtilisin Carlsberg, subtilisin 309, subtilisin 147, and subtilisin 168 (see, e.g., WO 89/06279). Exemplary proteases include but are not limited to those described in WO95/23221, WO92/21760, WO2008010925, WO20100566356, WO2011072099, WO201113022, WO2011140364, WO2012151534, WO2015038792, WO2015089441, WO2015089447, WO2015143360, WO2016001449, WO2016001450, WO2016061438, WO2016069544, WO2016069548, WO2016069552, WO 2016069557, WO2016069563, WO2016069569, WO2016087617, WO2016087619, WO2016145428, WO2016174234, WO2016183509, WO2016202835, WO2016205755, US 2008/0090747, U.S. Pat. Nos. 5,801,039, 5,340,735, 5,500,364, 5,855,625, RE 34,606, U.S. Pat. Nos. 5,955,340, 5,700,676, 6,312,936, 6,482,628, 8,530,219, U.S. Provisional Appl Nos. 62/331, 282, 62/343,618, 62/351,649, 62/437,171, 62/437,174, and 62/437,509, and PCT Appl Nos. PCT/CN2017/076749 and, as well as metalloproteases described in WO 2007/044993, WO 2009/058303, WO 2009/058661, WO 2014/071410, WO 2014/194032, WO 2014/194034, WO 2014/194054, and WO 2014/194117.

Exemplary commercial proteases include, but are not limited to MAXATASE, MAXACAL, MAXAPEM, OPTI-CLEAN®, OPTIMASE®, PROPERASE®, PURAFECT®,

US 12,584,119 B2

23

PURAFECT® OXP, PURAMAX®, EXCELLASE®, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST (Danisco US); ALCALASE®, ALCALASE® ULTRA, BLAZE®, BLAZE® EVITY®, BLAZE® EVITY® 16L, CORONASE®, SAVINASE®, SAVINASE® ULTRA, SAVINASE® EVITY®, SAVINASE® EVERTS®, PRIMASE, DURAZYM, POLARZYME®, OVOZYME®, KANNASE®, LIQUANASE®, EVERTS®, NEUTRASE®, PROGRESS UNO®, RELASE® and ESPERASE® (Novozymes); BLAP™ and BLAP™ variants (Henkel); LAVERGY™ PRO 104 L (BASF), and KAP® (B. alkalophilus subtilisin) (Kao). Suitable proteases include naturally occurring proteases or engineered variants specifically selected or engineered to work at relatively low temperatures.

Suitable lipases include those of bacterial or fungal origin. Chemically modified, proteolytically modified, or protein engineered mutants are included. Examples of useful lipases include but are not limited to lipases from Humicola (synonym Thermomyces), e.g., from H. lanuginosa (T. lanuginosus) (see e.g., EP 258068 and EP 305216), from H. insolens (see e.g., WO 96/13580); a Pseudomonas lipase (e.g., from P. alcaligenes or P. pseudoalcaligenes; see, e.g., EP 218 272), P. cepacia (see e.g., EP 331 376), P. stutzeri (see e.g., GB 1,372,034), P. fluorescens, Pseudomonas sp. strain SD 705 (see e.g., WO 95/06720 and WO 96/27002), P. wisconsinensis (see e.g., WO 96/12012); a Bacillus lipase (e.g., from B. subtilis; see e.g., Dartois et al. (1993) Biochemica et Biophysica Acta 1131:253-360), B. stearothermophilus (see e.g., JP 64/744992), or B. pumilus (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105.

Exemplary commercial lipases include, but are not limited to M1 LIPASE, LUMA FAST, and LIPOMAX (Genencor); LIPEX®, LIPOCLEAN®, LIPOLASE® and LIPOLASE® ULTRA (Novozymes); and LIPASE P (Amano Pharmaceutical Co. Ltd).

Polyesterases: Suitable polyesterases can be included in the composition, such as those described in, for example, WO 01/34899, WO 01/14629, and U.S. Pat. No. 6,933,140.

The present compositions can be combined with other amylases, including other α-amylases. Such a combination is particularly desirable when different α-amylases demonstrate different performance characteristics and the combination of a plurality of different α-amylases results in a composition that provides the benefits of the different α-amylases. Other amylases include commercially available amylases, such as but not limited to STAINZYME®, NATALASE®, DURAMYL®, TERMAMYL®, FUNGAMYL® and BAN™ (Novo Nordisk A/S and Novozymes A/S); RAPIDASE®, POWERASE®, PURASTAR®, and PREFERENZ™ (from DuPont Industrial Biosciences). Exemplary α-amylases are described in WO9418314A1, US20080293607, WO2013063460, WO10115028, WO2009061380A2, WO2014099523, WO2015077126A1, WO2013184577, WO2014164777, WO9510603, WO9526397, WO9623874, WO9623873, WO9741213, WO9919467, WO0060060, WO0029560, WO9923211, WO9946399, WO0060058, WO0060059, WO9942567, WO0114532, WO02092797, WO0166712, WO0188107,

24

WO0196537, WO0210355, WO2006002643, WO2004055178, and WO9813481.

Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed for example in U.S. Pat. Nos. 4,435,307; 5,648,263; 5,691,178; 5,776,757; and WO 89/09259. Exemplary cellulases contemplated for use are those having color care benefit for the textile. Examples of such cellulases are cellulases described in for example EP 0495257, EP 0531372, WO 96/11262, WO 96/29397, and WO 98/08940. Other examples are cellulase variants, such as those described in WO 94/07998; WO 98/12307; WO 95/24471; PCT/DK98/00299; EP 531315; U.S. Pat. Nos. 5,457,046; 5,686,593; and 5,763,254. Exemplary cellulases include those described in WO2005054475, WO2005056787, U.S. Pat. Nos. 7,449,318, 7,833,773, 4,435,307; EP 0495257; and U.S. Provisional Appl. Nos. 62/296,678 and 62/435,340. Exemplary commercial cellulases include, but are not limited to, CELLUCLEAN®, CELLUZYME®, CAREZYME®, CAREZYME® PREMIUM, ENDOLASE®, and RENOZYME® (Novozymes); REVITALENZ®100, REVITALENZ® 200/220 and REVITALENZ® 2000 (Danisco US); and KAC-500(B) (Kao Corporation).

Exemplary mannanases include, but are not limited to, those of bacterial or fungal origin, such as, for example, as is described in WO2016007929; U.S. Pat. Nos. 6,566,114, 6,602,842, and 6,440,991; and International Appl. Nos. PCT/US2016/060850 and PCT/US2016/060844. Exemplary mannanases include, but are not limited to, those of bacterial or fungal origin, such as, for example, as is described in WO2016007929; U.S. Pat. Nos. 6,566,114, 6,602,842, and 6,440,991; and International Appl. Nos. PCT/US2016/060850 and PCT/US2016/060844.

Suitable peroxidases/oxidases contemplated for use in the compositions include those of plant, bacterial or fungal origin. Chemically modified or protein engineered mutants are included. Examples of useful peroxidases include peroxidases from Coprinus, e.g., from C. cinereus, and variants thereof as those described in WO 93/24618, WO 95/10602, and WO 98/15257. Commercially available peroxidases include for example GUARDZYME™ (Novo Nordisk A/S and Novozymes A/S).

The detergent composition can also comprise 2,6-β-D-fructan hydrolase, which is effective for removal/cleaning of biofilm present on household and/or industrial textile/laundry.

The detergent enzyme(s) may be included in a detergent composition by adding separate additives containing one or more enzymes, or by adding a combined additive comprising all of these enzymes. A detergent additive, i.e. a separate additive or a combined additive, can be formulated, e.g., as a granulate, a liquid, a slurry, and the like. Exemplary detergent additive formulations include but are not limited to granulates, in particular non-dusting granulates, liquids, in particular stabilized liquids or slurries.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing about 30% or less water are also contemplated.

US 12,584,119 B2

25

Numerous exemplary detergent formulations to which the present amylases can be added (or is in some cases are identified as a component of) are described in WO2013063460. These include commercially available unit dose detergent formulations/packages such as PUREX® UltraPacks (Henkel), FINISH® Quantum (Reckitt Benckiser), CLOROX™ 2 Packs (Clorox), OxiClean Max Force Power Paks (Church & Dwight), TIDE® Stain Release, CASCADE® ActionPacs, and TIDE® Pods (Procter & Gamble), PS.

8.6. Methods of Assessing Amylase Activity in Detergent Compositions

Numerous α-amylase cleaning assays are known in the art, including swatch and micro-swatch assays. The appended Examples describe only a few such assays.

In order to further illustrate the compositions and methods, and advantages thereof, the following specific examples are given with the understanding that they are illustrative rather than limiting.

All references cited herein are herein incorporated by reference in their entirety for all purposes. In order to further illustrate the compositions and methods, and advantages thereof, the following specific examples are given with the understanding that they are illustrative rather than limiting.

EXAMPLES

Example 1: Methods

Structural Modeling of BspAmy24

A homology model of BspAmy24 was constructed as follows. The amino acid sequence of BspAmy24 (SEQ ID NO: 1) was used as a query in MOE (Chemical Computing Group, Montreal, CA) to search the public structure database. The Bacillus licheniformis alpha-amylase (1BLI) was the top public hit. The "homology model" function with all default parameters was used to create a model. An X-ray diffraction crystal structure was also determined for a BspAmy24 variant; this experimental structure closely matched the homology model and supported the analysis performed with the homology model.

Cell Growth and Protein Quantification

BspAmy24-V1 (having a deletion of residues R181 and G182) and variants of BspAmy24-V1 were expressed in Bacillus licheniformis cells after following standard cloning procedures to introduce appropriate DNA sequences. Cells were grown for 68 hours in expression medium suitable for secreted protein expression from B. licheniformis. Secreted protein was harvested by centrifugation followed by filtration through 0.45 μm membranes (EMD Millipore). In some cases, additional purification was performed using ion exchange chromatography with Phenyl Sepharose 6 Fast Flow resin (GE Healthcare). Protein concentration was determined by high performance liquid chromatography (HPLC) and absorbance at 280 nm.

Enzyme Performance Assay and Measurement of pK$_a$ Values

The activity of the α-amylases at different pH values was measured using a microswatch assay. In a 96-well microtiter plate containing two micro-swatches (CS28 starch stain with dye on cotton, Center for Testmaterials, Vlaardingen, Netherlands), diluted enzyme was added to buffer with 2 mM CaCl$_2$) and 0.005% Tween-80, total 200 μl reaction volume. The plate was incubated at 50° C. for 15 minutes with shaking at 1,150 rpm. The supernatant was then removed

26 from the swatch plate and the amount of dye released into the supernatant was quantified optically. The release of dye into the supernatant correlated with enzyme activity. The rate constant was determined at each pH and the plot of the log of the rate constant versus pH was fit to a single or double ionization model, as follows, where k$_{max}$ represents the maximum rate constant, pK$_a$, pK$_{a1}$, and pK$_{a2}$ represent pK$_a$ values for the enzyme, and pH represents the pH of the reaction:

$$\log k = \log\left(\frac{k_{max}}{1 + 10^{pH-pKa}}\right)$$

$$\log k = \log\left(\frac{k_{max}}{1 + 10^{pKa1-pH} + 10^{pH-pKa2}}\right)$$

Example 2: Results Obtained Using α-Amylase Variants pK$_a$ Values Measured for Four Variants For four variants (i.e., T40N, F261Y, S286D and Y362L), α-amylase activity at several pH values was measured and used to determine apparent pK$_a$ values from curve fits. All variants additionally included the deletion of residues R181 and G182 (the alternative deletion of adjacent residues T183 and G184 would be expected to produce similar results), which is a standard mutation in α-amylases. The rate constant of the enzyme was determined at each pH value and the plot of the log of rate constant versus pH was fit to a single or double ionization model. The results are shown in Table 3 and FIGS. 4-7. Amino acid numbering is given as deletion numbers, according the amino acid sequence of BspAmy24-V1, and non-deletion numbering, according the amino acid sequence of BspAmy24.

TABLE 3 pK$_a$ values for four variants

| Mutations in deletion numbering | Mutations in non-deletion numbering | pK$_a$ value obtained from curve fit |
|---|---|---|
| — | del-R181-G182 | 10.9 |
| T40N | T40N | 10.3 |
| F261Y | F263Y | 10.2 |
| S286D | S288D | 10.8 |
| Y362L | Y364L | 9.7 |

Activity Ratio for Seven Additional Variants

For seven additional variants, the activity was measured at pH 8.5 and pH 10.5 and the ratio of the activity at pH 8.5 compared to the activity at pH 10.5 was determined according to the formula ("WT" in this context is the del-R181-G182 molecule):

$$\frac{\left(\frac{pH\ 8.5}{pH\ 10.5}\right)_{mutant}}{\left(\frac{pH\ 8.5}{pH\ 10.5}\right)_{WT}}$$

The data in Table 4 show that these additional mutations have increased activity ratios relative to the wild type enzyme.

TABLE 4

| | Activity ratios for seven additional variants | |
| --- | --- | --- |
| Mutations in deletion numbering | Mutations in non-deletion numbering | Activity ratio |
| None | del-R181-G182 | 1.0 |
| T40C | T40C | 1.2 |
| T40D | T40D | 4.9 |
| T40E | T40E | 2.0 |
| F261P | F263P | 1.4 |

5

TABLE 4-continued

| | Activity ratios for seven additional variants | |
| --- | --- | --- |
| Mutations in deletion numbering | Mutations in non-deletion numbering | Activity ratio |
| S286K | S288K | 1.1 |
| Y362E | Y364E | 1.4 |
| Y362M | Y364M | 5.8 |

SEQUENCE LISTING

```
<160> NUMBER OF SEQ ID NOS: 3

<210> SEQ ID NO 1
<211> LENGTH: 486
<212> TYPE: PRT
<213> ORGANISM: Bacillus sp.

<400> SEQUENCE: 1

His His Asn Gly Thr Asn Gly Thr Met Met Gln Tyr Phe Glu Trp His
1               5                   10                  15

Leu Pro Asn Asp Gly Gln His Trp Asn Arg Leu Arg Asn Asp Ala Ala
            20                  25                  30

Asn Leu Lys Asn Leu Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Ser Gln Leu Gln Ser Ala Ile Ala Ser Leu Gln Asn Asn Gly
                85                  90                  95

Ile Gln Val Tyr Gly Asp Val Val Met Asn His Lys Gly Gly Ala Asp
                100                 105                 110

Gly Thr Glu Trp Val Gln Ala Val Glu Val Asn Pro Ser Asn Arg Asn
            115                 120                 125

Gln Glu Val Thr Gly Glu Tyr Thr Ile Glu Ala Trp Thr Lys Phe Asp
        130                 135                 140

Phe Pro Gly Arg Gly Asn Thr His Ser Ser Phe Lys Trp Arg Trp Tyr
145                 150                 155                 160

His Phe Asp Gly Thr Asp Trp Asp Gln Ser Arg Gln Leu Asn Asn Arg
                165                 170                 175

Ile Tyr Lys Phe Arg Gly Thr Gly Lys Ala Trp Asp Trp Glu Val Asp
                180                 185                 190

Thr Glu Asn Gly Asn Tyr Asp Tyr Leu Met Tyr Ala Asp Val Asp Met
            195                 200                 205

Asp His Pro Glu Val Ile Asn Glu Leu Arg Arg Trp Gly Val Trp Tyr
        210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Asn His Val Arg Ser Thr
                245                 250                 255

Thr Gly Lys Asn Asn Met Phe Ala Val Ala Glu Phe Trp Lys Asn Asp
            260                 265                 270

Leu Gly Ala Ile Glu Asn Tyr Leu His Lys Thr Asn Trp Asn His Ser
        275                 280                 285
```

```
Val Phe Asp Val Pro Leu His Tyr Asn Leu Tyr Asn Ala Ser Lys Ser
    290                 295                 300

Gly Gly Asn Tyr Asp Met Arg Gln Ile Leu Asn Gly Thr Val Val Ser
305                 310                 315                 320

Lys His Pro Ile His Ala Val Thr Phe Val Asp Asn His Asp Ser Gln
                325                 330                 335

Pro Ala Glu Ala Leu Glu Ser Phe Val Glu Ala Trp Phe Lys Pro Leu
                340                 345                 350

Ala Tyr Ala Leu Ile Leu Thr Arg Glu Gln Gly Tyr Pro Ser Val Phe
                355                 360                 365

Tyr Gly Asp Tyr Tyr Gly Ile Pro Thr His Gly Val Ala Ala Met Lys
    370                 375                 380

Gly Lys Ile Asp Pro Ile Leu Glu Ala Arg Gln Lys Tyr Ala Tyr Gly
385                 390                 395                 400

Thr Gln His Asp Tyr Leu Asp His His Asn Ile Ile Gly Trp Thr Arg
                405                 410                 415

Glu Gly Asn Ser Ala His Pro Asn Ser Gly Leu Ala Thr Ile Met Ser
                420                 425                 430

Asp Gly Pro Gly Gly Ser Lys Trp Met Tyr Val Gly Arg His Lys Ala
                435                 440                 445

Gly Gln Val Trp Arg Asp Ile Thr Gly Asn Arg Thr Gly Thr Val Thr
    450                 455                 460

Ile Asn Ala Asp Gly Trp Gly Asn Phe Ser Val Asn Gly Gly Ser Val
465                 470                 475                 480

Ser Ile Trp Val Asn Lys
                485
```

```
<210> SEQ ID NO 2
<211> LENGTH: 485
<212> TYPE: PRT
<213> ORGANISM: Bacillus sp. 707

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
            115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175
```

```
Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
            195                 200                 205

Asp His Pro Glu Val Val Asn Glu Leu Arg Asn Trp Gly Val Trp Tyr
        210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
            275                 280                 285

Phe Asp Val Pro Leu His Tyr Asn Leu Tyr Asn Ala Ser Lys Ser Gly
        290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Arg Ser
        370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
            435                 440                 445

Gln Val Trp Ser Asp Ile Thr Gly Asn Arg Thr Gly Thr Val Thr Ile
        450                 455                 460

Asn Ala Asp Gly Trp Gly Asn Phe Ser Val Asn Gly Gly Ser Val Ser
465                 470                 475                 480

Ile Trp Val Asn Lys
                485
```

<210> SEQ ID NO 3
<211> LENGTH: 485
<212> TYPE: PRT
<213> ORGANISM: Bacillus sp. AA560

<400> SEQUENCE: 3

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
```

-continued

```
      50                   55                   60

Asp Leu Gly Glu Phe Asn Gln Lys Gly Thr Ile Arg Thr Lys Tyr Gly
65                   70                   75                   80

Thr Arg Asn Gln Leu Gln Ala Ala Val Asn Ala Leu Lys Ser Asn Gly
                85                   90                   95

Ile Gln Val Tyr Gly Asp Val Val Met Asn His Lys Gly Gly Ala Asp
                100                  105                  110

Ala Thr Glu Met Val Arg Ala Val Glu Val Asn Pro Asn Asn Arg Asn
        115                  120                  125

Gln Glu Val Ser Gly Glu Tyr Thr Ile Glu Ala Trp Thr Lys Phe Asp
        130                  135                  140

Phe Pro Gly Arg Gly Asn Thr His Ser Asn Phe Lys Trp Arg Trp Tyr
145                  150                  155                  160

His Phe Asp Gly Val Asp Trp Asp Gln Ser Arg Lys Leu Asn Asn Arg
                165                  170                  175

Ile Tyr Lys Phe Arg Gly Asp Gly Lys Gly Trp Asp Trp Glu Val Asp
                180                  185                  190

Thr Glu Asn Gly Asn Tyr Asp Tyr Leu Met Tyr Ala Asp Ile Asp Met
        195                  200                  205

Asp His Pro Glu Val Val Asn Glu Leu Arg Asn Trp Gly Val Trp Tyr
        210                  215                  220

Thr Asn Thr Leu Gly Leu Asp Gly Phe Arg Ile Asp Ala Val Lys His
225                  230                  235                  240

Ile Lys Tyr Ser Phe Thr Arg Asp Trp Ile Asn His Val Arg Ser Ala
                245                  250                  255

Thr Gly Lys Asn Met Phe Ala Val Ala Glu Phe Trp Lys Asn Asp Leu
                260                  265                  270

Gly Ala Ile Glu Asn Tyr Leu Asn Lys Thr Asn Trp Asn His Ser Val
                275                  280                  285

Phe Asp Val Pro Leu His Tyr Asn Leu Tyr Asn Ala Ser Lys Ser Gly
        290                  295                  300

Gly Asn Tyr Asp Met Arg Gln Ile Phe Asn Gly Thr Val Val Gln Arg
305                  310                  315                  320

His Pro Met His Ala Val Thr Phe Val Asp Asn His Asp Ser Gln Pro
                325                  330                  335

Glu Glu Ala Leu Glu Ser Phe Val Glu Glu Trp Phe Lys Pro Leu Ala
                340                  345                  350

Tyr Ala Leu Thr Leu Thr Arg Glu Gln Gly Tyr Pro Ser Val Phe Tyr
        355                  360                  365

Gly Asp Tyr Tyr Gly Ile Pro Thr His Gly Val Pro Ala Met Lys Ser
        370                  375                  380

Lys Ile Asp Pro Ile Leu Glu Ala Arg Gln Lys Tyr Ala Tyr Gly Arg
385                  390                  395                  400

Gln Asn Asp Tyr Leu Asp His His Asn Ile Ile Gly Trp Thr Arg Glu
                405                  410                  415

Gly Asn Thr Ala His Pro Asn Ser Gly Leu Ala Thr Ile Met Ser Asp
                420                  425                  430

Gly Ala Gly Gly Asn Lys Trp Met Phe Val Gly Arg Asn Lys Ala Gly
                435                  440                  445
```

-continued

```
Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485
```

What is claimed is:

1. A recombinant variant of a parental Family 13 α-amylase, the variant having at least 95% amino acid sequence identity to the amino acid sequence of SEQ ID NO: 1 and having an amino acid mutation in an amino acid residue that lines the N-terminal side of the core β-barrel structure of the α-amylase that results in the variant having an amino acid residue that is different from the naturally occurring amino acid in the parent α-amylase, and which results in reduction of the apparent pK$_a$ value of the general acid and an increase in the activity of the variant at a pH between about 8.5 and 10.5, wherein the mutation is an amino acid substitution at a position selected from the group consisting of T40C, T40D, T40E, F263P, F263Y, S288D, S288K, Y364E, and Y364L corresponding to the amino acid sequence of SEQ ID NO: 1, and wherein the variant comprises a deletion of residues 181 and 182 corresponding to positions 181 and 182 in the amino acid sequence of SEQ ID NO: 1.

2. The variant α-amylase of claim 1, wherein the ratio of the activity at pH 8.5 compared to the activity at pH 10.5 for the variant divided by the ratio of the activity at pH 8.5 compared to the activity at pH 10.5 of an otherwise identical α-amylase lacking the amino acid mutation in an amino acid residue that lines the N-terminal side of the core β-barrel structure of the α-amylase is greater than 1, greater than 2, greater than 3, or greater than 4.

3. The variant α-amylase of claim 1, further comprising:
(i) any single, multiple or combinatorial mutation(s) previously described in a Family 13 α-amylase; and/or
(ii) an N-terminal and/or C-terminal truncation.

4. The variant α-amylase of claim 1, having at least amino acid sequence identity to the amino acid sequence of SEQ ID NO: 1.

5. A method for modulating the activity of an α-amylase comprising introducing into a parental Family 13 α-amylase having at least 95% amino acid sequence identity to the amino acid sequence of SEQ ID NO: 1 a mutation of a residue that affects the electrostatic environment of the general acid positioned for catalysis, wherein the mutation is located at the N-terminal side of the α-amylase β-barrel, and wherein the mutation changes the electrostatic environment of the general acid in the resulting variant α-amylase, wherein the mutation is an amino acid substitution at a position selected from the group consisting of T40C, T40D, T40E, F263P, F263Y, S288D, S288K, Y364E, and Y364L corresponding to the amino acid sequence of SEQ ID NO: 1, and wherein the variant comprises a deletion of residues 181 and 182 corresponding to positions 181 and 182 in the amino acid sequence of SEQ ID NO: 1.

6. The method of claim 5, wherein the ratio of the activity of the variant α-amylase at pH 8.5 compared to the activity at pH 10.5 divided by the ratio of the activity at pH 8.5 compared to the activity at pH 10.5 of an otherwise identical α-amylase lacking the amino acid mutation in an amino acid residue that lines the N-terminal side of the core β-barrel structure of the α-amylase is greater than 1, greater than 2, greater than 3, or greater than 4.

7. The method of claim 5, wherein the variant α-amylase further comprises:
(i) any single, multiple or combinatorial mutation(s) previously described in a Family 13 α-amylase; and/or
(ii) an N-terminal and/or C-terminal truncation.

8. A composition for liquefying starch comprising the variant α-amylase of claim 1.

9. A detergent composition comprising the variant amylase of claim 1.

10. A method for converting starch to oligosaccharides, comprising contacting starch with effective amount of the variant amylase of claim 1.

11. A method for removing a starchy stain or soil from a surface, comprising contacting the surface with an effective amount of the variant amylase of claim 1, and allowing the polypeptide to hydrolyze starch components present in the starchy stain to produce smaller starch-derived molecules that dissolve in the aqueous composition, thereby removing the starchy stain from the surface.

12. The composition of claim 9, further comprising a protease.

* * * * *